United States Patent
Gildert et al.

(10) Patent No.: US 6,274,783 B1
(45) Date of Patent: Aug. 14, 2001

(54) CATALYTIC DISTILLATION PROCESS FOR THE PRODUCTION OF $C_8$ ALKANES

(75) Inventors: Gary R. Gildert; Mitchell E. Loescher, both of Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 09/531,288

(22) Filed: Mar. 20, 2000

(51) Int. Cl.[7] ............... C07C 2/74; C07C 2/04
(52) U.S. Cl. .......... 585/255; 585/510; 585/533; 203/DIG. 6
(58) Field of Search .............. 585/510, 533, 585/255; 203/DIG. 6

(56) References Cited

U.S. PATENT DOCUMENTS

| | | | |
|---|---|---|---|
| 3,728,415 | 4/1973 | Arganbright | 260/683.15 R |
| 3,758,626 | 9/1973 | Arganbright et al. | 260/683.15 R |
| 3,960,978 | 6/1976 | Givens et al. | 260/683.15 R |
| 4,021,502 | 5/1977 | Plank et al. | 260/683.15 R |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |
| 4,242,530 | 12/1980 | Smith, Jr. | 585/510 |
| 4,950,834 | 8/1990 | Arganbright et al. | 585/446 |
| 5,003,124 | 3/1991 | Smith, Jr. et al. | 585/526 |
| 5,321,163 | 6/1994 | Hickey et al. | 568/59 |
| 5,510,555 | 4/1996 | Brunelli et al. | 585/508 |
| 5,595,634 | 1/1997 | Hearn et al. | 203/29 |
| 5,608,133 | 3/1997 | Chang et al. | 585/524 |

Primary Examiner—Marian C. Knode
Assistant Examiner—Thuan D. Dang
(74) Attorney, Agent, or Firm—Kenneth H. Johnson

(57) ABSTRACT

A process is disclosed for the concurrent production and hydrogenation of diisobutene in a single distillation column reactor containing both a dimerization catalyst and a hydrogenation catalyst by the dimerized of isobutene to diisobutene. The catalysts may be in alternating beds or physically mixed together in one or more beds. Alternatively a bifunctional catalyst having both dimerization and hydrogenation properties may be used.

12 Claims, 1 Drawing Sheet

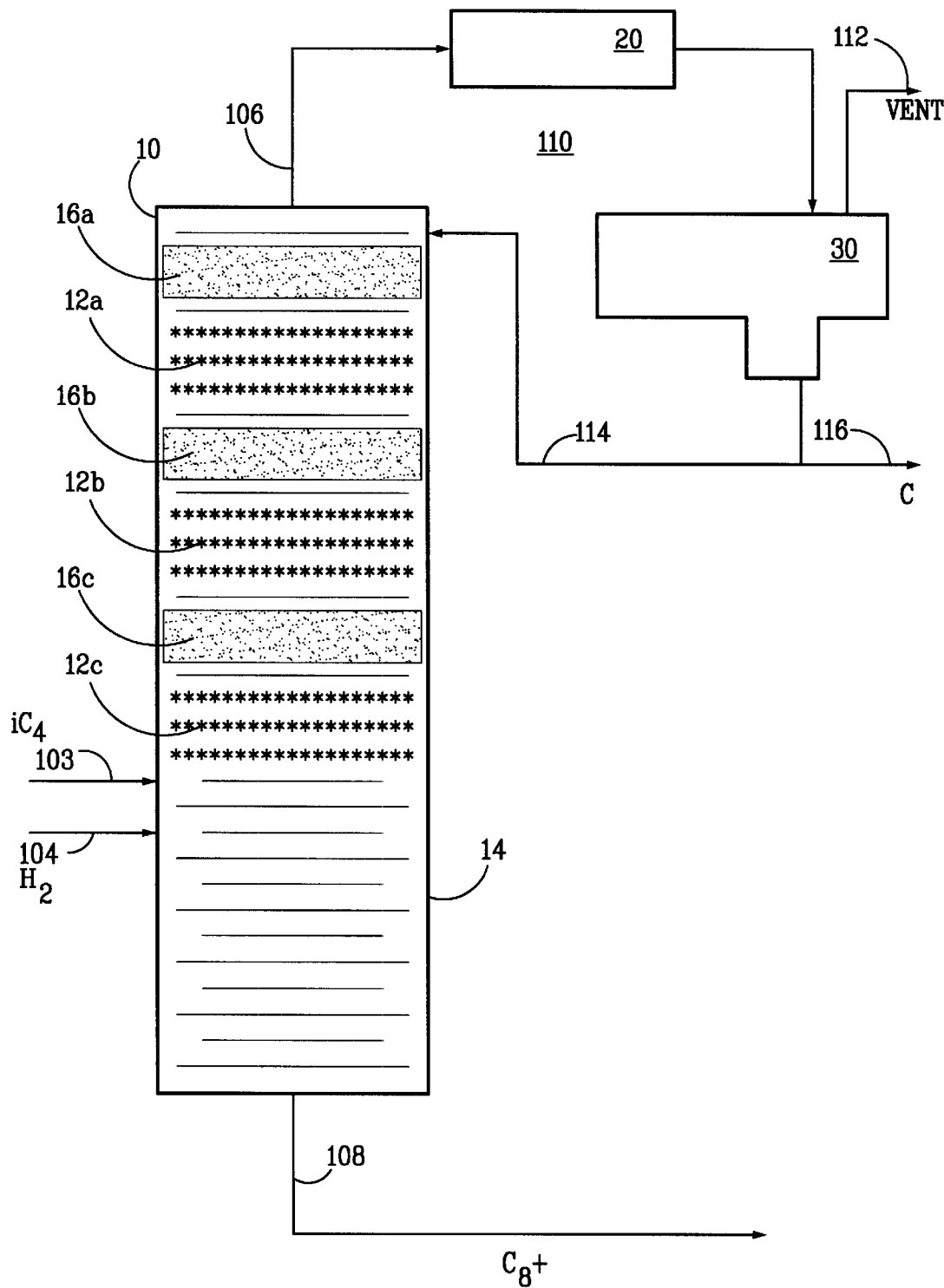
FIGURE

CATALYTIC DISTILLATION PROCESS FOR THE PRODUCTION OF $C_8$ ALKANES

BACKGROUND OF THE INVENTION

1. Field of the Invention

The present invention relates generally to a process for the concurrent production and hydrogenation of diisobutene. More particularly the invention relates to a process wherein isobutylene is dimerized and hydrogenated in a single distillation column reactor to produce desirable gasoline blending stocks, specifically the single step process produces 2,2,4-trimethyl pentane (isooctane). The resultant product which may be a mixture of isooctane, other $C_8$ alkanes or alkenes is a superior blending stock for producing gasolines, including the CARB specifications.

2. Related Art

Conversion of olefins to gasoline and/or distillate products is disclosed in U.S. Pat. Nos. 3,960,978 and 4,021,502 wherein gaseous olefins in the range of ethylene to pentene either alone or in admixture with paraffins are converted into an olefinic gasoline blending stock by contacting the olefins with a catalyst bed made up of a ZSM-5 type zeolite. In U.S. Pat. No. 4,227,992, Garwood and Lee disclose operating conditions for the selective conversion of $C_3+$ olefins mainly to aliphatic hydrocarbons. Also, U.S. Pat. Nos. 4,150,062 and 4,211,640 disclose a process for converting olefins to gasoline components. Chang, et al, in U.S. Pat. No. 5,608,133 disclose production of synthetic lubricants by oligomerization of $C_2$–$C_5$ olefins and subsequent hydrogenation of the higher boiling olefins. A liquid phase process for the oligomerization of $C_4$ and $C_5$ isoolefins is disclosed in U.S. Pat. No. 5,003,124 wherein the reaction mixture is allowed to boil to remove the heat of reaction and a further dimerization is obtained in a reactive distillation column. U.S. Pat. No. 4,242,124 Smith discloses the reaction of isobutene with itself in a catalytic distillation column reactor to form diisobutene.

Brunelli, et al, in U.S. Pat. No. 5,510,555 disclose that the two isomers of diisobutene, 2,4,4-tri-methyl pentene and 2,4,4-tri-methyl-2-pentene when hydrogenated both yield 2,2,4 tri-methyl pentane which is the standard for octane measurement, i.e., RON=100 and MON=100.

Isooctane is not known to have been produced in a single step process of concurrent dimerization and hydrogenation heretofore.

SUMMARY OF THE INVENTION

Briefly the present invention comprises the concurrent dimerization of isobutene and the hydrogenation of the resultant diisobutene in a single distillation column reactor. Catalysts useful for the dimerization reaction include acidic cation exchange resins and zeolites. The hydrogenation catalysts are preferably Group VIII metals preferably deposited on carrier or support, such as an alumina, and include, among others, platinum, nickel, palladium and cobalt. The catalysts may be placed in the distillation column reactor in alternating layers or physically mixed. Alternatively bifunctional catalysts may be used, such as cation resins having palladium complexes deposited thereon.

The isobutene may be fed along with a hydrogen stream to a reaction distillation column at an effectuating hydrogen partial pressure of at least about 0.1 psia to less than 70 psia, such as less than 50 psia to a reactive distillation containing both a dimerization catalyst and a hydrogenation catalyst both of which are preferably components of a distillation structure. A portion of the diisobutene is selectively hydrogenated. Within the hydrogen partial pressures as defined no more hydrogen than necessary to maintain the catalyst and hydrogenate the olefinic compounds is employed, since the excess hydrogen is usually vented. In addition to the concurrent dimerization and hydrogenation there is also a concurrent fractionation of the reaction mixture within the reactive distillation zone.

The $C_4$ feed containing the isobutene is preferably maintained within the catalyst bed or beds. As in any distillation, the composition of a fraction within a section of the column, e.g., a catalyst bed can be controlled by adjusting the pressure in the column pressure, in so doing the isobutene is selectively dimerized and hydrogenated and the higher boiling $C_8$ product is fractionated downward from the catalyst bed. Some of the isobutene may be hydrogenated before it is dimerized and the lower boiling $C_4$ alkanes are fractionated upward out of the catalyst bed.

The term "reactive distillation" is used to describe the concurrent reaction and fractionation in a column. For the purposes of the present invention, the term "catalytic distillation" includes reactive distillation and any other process of concurrent reaction and fractional distillation in a column, i.e., a distillation column reactor, regardless of the designation applied thereto.

The catalyst beds as used in the present invention may be described as fixed, meaning positioned in a fixed area of the column and include expanded beds and ebulating beds of catalysts. The catalysts in the beds may all be the same or different so long as they carry out the functions of dimerization and hydrogenation as described. Catalysts prepared as distillation structures are particularly useful in the present invention.

BRIEF DESCRIPTION OF THE DRAWING

The FIGURE is a flow diagram in schematic form of one embodiment of the invention.

DETAILED DESCRIPTION OF THE INVENTION

Isobutene is dimerized to diisobutene according to the following reaction:

The dimerization of isobutene with itself is of particular interest because either of the isomers of diisobutene produce 2,2,4-trimethyl pentane (isooctane) when hydrogenated. The presence of the Group VIII metals and hydrogen may also produce some bond and/or skeletal isomerization.

The catalytic material employed in the process is preferably in a form to serve as distillation packing. Broadly stated, the catalytic material is preferably a component of a distillation system functioning as both a catalyst and distillation packing, i.e., a packing for a distillation column having both a distillation function and a catalytic function. The catalyst is prepared in the form of a catalytic distillation structure.

The dimerization catalyst may include either an acidic cation exchange resin or zeolite, which are generally employed as fine powders. Structures for this use are described in U.S. Pat. Nos. 4,215,011, 4,302,356; 4,443,559; 5,266,546 and 5,348,710 which are incorporated herein. Other catalytic distillation structures useful for this purpose are disclosed in U.S. Pat. Nos. 4,731,229; 5,073,236; 5,431,890 and 5,730,843 which are also incorporated by reference. One multifunctional catalytic distillation structure is disclosed in commonly owned U.S. Pat. Nos. 5,942,456 which is incorporated herein by reference.

The mole sieve or cation exchange resin catalyst packing is of such a nature as to allow vapor flow through the bed, yet provide a sufficient surface area for catalytic contact as described in the previously noted patents. The catalyst packing is preferably arranged in the upper portion of the distillation column reactor, more preferably occupying about one-third to one half of the column. A rectification section may be located above the catalyst zone.

The hydrogenation catalyst generally comprises a Group VIII metal supported on an alumina carrier in the form of extrudates or spheres. The extrudates or spheres are placed in porous containers, as described in the above for the cation exchange resin and suitably supported in the distillation column reactor to allow vapor flow through the bed yet provide a sufficient surface area for catalytic contact.

Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures.

The reaction system can be described as heterogenous since the catalyst remains a distinct entity. Any suitable hydrogenation catalyst may be used, for example Group VIII metals of the Periodic Table of Elements as the principal catalytic component, alone or with promoters and modifiers such as palladium/gold, palladium/silver, cobalt/zirconium, nickel, which are preferably deposited on a support such as alumina, fire brick, pumice, carbon, silica, resin or the like.

The intermixing of the different catalyst components in a single bed or series of beds is a preferred embodiment.

To provide the desired degree of temperature and residence time control, a process and apparatus are provided wherein the reaction liquid is boiling within a distillation column reactor. Overheads are withdrawn and condensed with some of the condensate being returned to the distillation column reactor as reflux. The advantage of the present process is that due to the continual reflux a portion of the selected dimer (diisobutene) is always condensing on the catalyst structure.

In the distillation column reactor it is believed that the effectiveness of the hydrogenation process may be the result of the condensation of a portion of the vapors in the reaction system which occludes sufficient hydrogen in the condensed liquid to obtain the requisite intimate contact between the hydrogen and the selected oligomers in the presence of the catalyst to result in their hydrogenation. The vaporization of the liquid feed removes a substantial amount of the exothermic heat of reaction. Since the liquid is at the boiling point in the reactor, the temperature may be controlled by the pressure. An increase in pressure increases the temperature and a decrease in pressure decreases the temperature.

Several different arrangements have been disclosed to achieve the desired result. For example, British Patents 2,096,603 and 2,096,604 disclose placing the catalyst on conventional trays within a distillation column. A series of U.S. patents, including those listed above and more, particularly U.S. Pat. Nos. 4,443,559 and 4,215,011 disclose using the catalyst as part of the packing in a packed distillation column. The use of multiple beds in a reaction distillation tower is also known and illustrated, for example, in U.S. Pat. Nos. 4,950,834; 5,321,163; and 5,595,634.

The catalyst component may take several forms. In the case of particulate catalytic material, generally from 60 mm to about 1 mm down through powders, is enclosed in a porous container such as screen wire or polymeric mesh. The material used to make the container must be inert to the reactants and conditions in the reaction system. The screen wire may be aluminum, steel, stainless steel, and the like. The polymer mesh may be nylon, Teflon, or the like. The mesh or threads per inch of the material used to make the container is such that the catalyst is retained therein and will not pass through the openings in the material. Catalyst particles of about 0.15 mm size or powders may be used and particles up to about ¼ inch diameter may be employed in the containers.

The dimerization catalyst and the hydrogenation catalyst may be present in any ratio, however volume ratios of 10:90 to 90:10 are preferred, with volume ratios of 40:60 to 60:40 being more preferred.

The reaction conditions in the distillation column reactor must be sufficient to first dimerize the isobutene and then hydrogenate the dimer to the alkane. The conditions are those in which the dimerization reaction is more selective than the hydrogenation. The conditions of pressure and temperature are those to hydrogenate only the dimer, e.g., 150° F. to a maximum temperature of 170–200° F. at 10 to 200 psig at the low hydrogen partial pressures described. To hydrogenate the mono olefins more severe conditions are required, e.g., 200–350° F., at 30 to 150 psig.

Referring now to the FIGURE a simplified flow diagram of one embodiment of the invention is shown. The feed containing the isobutene to be dimerized is fed via flow line 103 to a distillation column reactor 10 containing alternating beds of acidic cation exchange resin 16a, 16b and 16c and hydrogenation catalyst 12a, 12b, and 12c. The catalyst in the bed alternatively could be physically mixed or be bifunctional.

Hydrogen is fed to a distillation column reactor via flow line 104. A portion of the isobutene is dimerized by the acidic cation exchange resin and then a portion of the resultant diisobutene is then hydrogenated to 2,2,4 tri-methyl pentane (isooctane). The unreacted isobutene is withdrawn from the distillation column reactor as overheads via flow line 106 and the condensible material condensed in overhead condenser 20. The condensed isobutene is separated from the hydrogen and collected in receiver 30. The unreacted hydrogen is vented via flow line 112 for possible reuse. A portion of the condensed isobutene is returned to the distillation column reactor 10 as reflux via flow line 114 while the remainder is removed via flow line 116. The diisobutene and isooctane are removed as bottoms via flow line 108.

The invention claimed is:

1. A process for producing $C_8$ alkane comprising:
   (a) feeding isobutene and hydrogen to a distillation column reactor containing a dimerization catalyst and a hydrogenation catalyst; and
   (b) concurrently in said distillation column reactor:
      (i) contacting said isobutene with said dimerization catalyst under conditions to preferentially react a portion of said isobutene with itself to produce diisobutene,
      (ii) contacting said diisobutene with hydrogen in the presence of said hydrogenation catalyst to produce $C_8$ alkane, and
      (iii) separating unreacted isobutene and diisobutene and $C_8$ alkane by fractional distillation.

2. The process according to claim 1 comprising
   (c) removing said unreacted isobutene and unreacted hydrogen from said distillation column reactor as overheads and (d) removing said diisobutene and said $C_8$ alkane from said distillation column reactor as bottoms.

3. The process according to claim 1 where said unreacted isobutene is condensed and a portion of said condensed isobutene is returned to said distillation column reactor as reflux.

4. The process according to claim 1 wherein the hydrogen partial pressure in the distillation column reactor is between 0.1 and 70 psia.

5. The process according to claim 1 wherein the total pressure is adjusted such that the temperature within said distillation column reactor is in the range of 150 to 300° F.

6. The process according to claim 1 wherein said dimerization catalyst and said hydrogenation catalyst are contained in alternating beds within said distillation column reactor.

7. The process according to claim 1 wherein said dimerization catalyst and said hydrogenation catalyst are physically mixed in one or more beds in said distillation column reactor.

8. The process according to claim 1 wherein said dimerization catalyst comprises an acidic cation exchange resin.

9. The process according to claim 1 wherein said dimerization catalyst comprises zeolite.

10. The process according to claim 1 wherein said hydrogenation catalyst comprises the oxide of a Group VIII metal supported on an alumina base or carbon base.

11. The process according to claim 4 wherein said column pressure is in the range of 10 to 250 psig.

12. The process according to claim 1 wherein the volume ratio of dimerization catalyst to hydrogenation catalyst is in the range of 10:90 to 90:10.

* * * * *